(12) United States Patent
Chekanov

(10) Patent No.: US 6,201,991 B1
(45) Date of Patent: Mar. 13, 2001

(54) METHOD OF PREVENTION AND TREATMENT OF ATHEROSCLEROSIS AND ARTICLE OF MANUFACTURE THEREFOR

(75) Inventor: Valeri S. Chekanov, Franklin, WI (US)

(73) Assignee: Heart Care Associates, LLC, Milwaukee, WI (US)

( * ) Notice: Subject to any disclaimer, the term of this patent is extended or adjusted under 35 U.S.C. 154(b) by 0 days.

(21) Appl. No.: 09/307,149

(22) Filed: May 7, 1999

(51) Int. Cl.$^7$ .................................................. A61N 1/00

(52) U.S. Cl. ................................................ 607/2; 607/72

(58) Field of Search ............................. 607/2, 3, 46, 48, 607/50, 72–74, 115, 116; 606/41; 128/898

(56) References Cited

U.S. PATENT DOCUMENTS

| Re. 33,925 | * | 5/1992 | Bales et al. ............................. 606/48 |
| 5,178,620 | * | 1/1993 | Eggers et al. .......................... 606/41 |
| 5,603,731 | * | 2/1997 | Whitney ................................. 607/121 |
| 5,609,617 | * | 3/1997 | Shealy et al. ........................... 607/68 |
| 5,876,397 |   | 3/1999 | Edelman et al. . |
| 6,023,640 | * | 2/2000 | Ross .......................................... 607/2 |

OTHER PUBLICATIONS

Grimm et al., "Symptoms, cardiovascular risk profile and spontaneous ECG in paced patients: a five year follow–up study," *Pacing Clin. Electrophysiol.* Dec. 1990;13(12 Pt 2):2086–90.

Moreira et al., "Survival Improvement with Dynamic Cardiomyoplasty in Patients With Dilated Cardiomyopathy," *Circulation* 1991;84[suppl III]:III–296–III–302.

Chiu et al., "Dynamic Cardiomyoplasty: An Overview," *Pace* 14:577–584 (1991).

Ko et al., "Isolated coronary artery bypass grafting in one hundred consecutive octogenarian patients. A multivariate analysis." *J Thorac Cardiovasc Surg* Oct. 1991;102(4):532–8.

Jelic, et al., "Survival in 1,431 pacemaker patients: prognostic factors and comparison with the general population." *Pacing Clin Electrophysiol* Feb. 1992;15(2):141–7.

Hochleitner et al., "Long–term efficacy of physiologic dual–chamber pacing in the treatment of end–stage idiopathic dilated cardiomyopathy." *Am J Cardiol* Nov. 15, 1992;70(15):1320–5.

Rosenqvist et al., "Survival in patients with permanent pacemakers." *Cardiol Clin* Nov. 1992;10(4):691–703.

Carpentier et al., "Dynamic cardiomyoplasty at seven years." *J Thorac Cardiovasc Surg* 1993;106:42–54.

Magovern et al., "Operation for Congestive Heart Failure: Transplantation, Coronary Artery Bypass, and Cardiomyoplasty." *Ann Thorac Surg* 1993;56:418–25.

Chiu et al., "Responses to Dynamic Cardiomyoplasty for Idiopathic Dilated Cardiomyopathy," *Am J Cardiol* Aug. 15, 1993;72.

Moreira et al., "Current Expectations in Dynamic Cardiomyoplasty," *Ann Thorac Surg* 1993;55:299–303.

Magovern et al., "Early Effects of Right Latissimus Dorsi Cardiomyoplasty on Left Ventricular Function," *Circulation* 1993;88[part 2]:298–303.

(List continued on next page.)

*Primary Examiner*—Jeffrey R. Jastrzab
(74) *Attorney, Agent, or Firm*—Nicholas A. Kees; Godfrey & Kahn, S.C.

(57) ABSTRACT

A method and system for preventing or treating atherosclerosis are provided in which a blood vessel susceptible to or containing atherosclerotic plaque is subjected to a low-frequency electrical impulse at an effective rate and amplitude to prevent or impede the establishment or decrease the size of the plaque in the vessel. The system can be implanted into the body of a patient or applied externally to the skin.

37 Claims, 1 Drawing Sheet

OTHER PUBLICATIONS

Chida et al., "Long–term follow–up study after permanent pacemaker implantation in patients aged 60 years or over with sick sinus syndrome," *Nippon Ronen Igakkai Zasshi* Oct. 1993;30(10):869–78 (English Abstract).

Chekanov et al., "Cardiomyoplasty Review of Early and Late Results," *Vascular Surgery* Sep. 1994;28–7.

Jagaden et al., "Late Hemodynamic Results After Cardiomyoplasty in Congestive Heart Failure," *Ann Thorac Surg* 1994;57:1151–7.

Shen et al., "Long–term survival after pacemaker implantation for heart block in patients > or = 65 years," *Am J Cardiol* Sep. 15, 1994;74(6):560–4 (English Abstract).

Ray et al., "Stability of the DDD pacing mode in patients 80 years of age and older," *Pacing Clin Electrophysiol* Jul. 1994;17(7):1218–21.

Tung et al., "Long–term survival after permanent pacemaker implantation for sick sinus syndrome," *Am J Cardiol* Nov. 15, 1994;74(10):1016–20.

Leitch et al., "Upward bias in estimates of pacemaker reliability: effect of unreported patient mortality," *J Am Coll Cardiol* Oct. 1994;24(4):1078–81.

Hagege et al., "Clinical Study of the Effects of Latissimus Dorsi Muscle Flap Stimulation After Cardiomyplasty," *Circulation* 1995;92[suppl II]:II–210–II–215.

Lange et al., "Treatment of Dilated Cardiomyopathy With Dynamic Cardiomyoplasty: The Heidelberg Experience," *Ann Thorac Surg* 1995;60:1219–25.

Moreira et al., "Present Trends in Clinical Experience with Dynamic Cardiomyoplasty," *Artif Organs,* vol. 19, No. 3, 1995.

Moreira et al., "Clinical and left ventricular function outcomes up to five years after dynamic cardiomyoplasty," *J Thorac Cardiovasc Surg* 1995;109:353–63.

Mattioli et al., "Causes of death in patients with unipolar single chamber ventricular packing: prevalence and circumstances in dependence on arrhythmias leading to pacemaker implantation," *Pacing Clin Electrophysiol* Jan. 1995;18(1 Pt 1):11–7.

Lamas et al., "Permanent pacemaker selection and subsequent survival in elderly Medicare pacemaker recipients," *Circulation* Feb 15, 1995;91(4):1063–9.

Dumcius et al., "Electrostimulated Cardiomyoplasty: From Experimental to Clinical Studies," *Pace* 1996 19:1205–1210.

Magovern et al., "Clinical Cardiomyoplasty: Review of the Ten–Year United States Experience," *Ann Thorac Surg* 1996;61:413–9.

Furnary et al., "Long–term outcome, survival analysis, and risk stratification of dynamic cardiomyoplasty," *J Thorac Cardiovasc Surg* 1996;112:1640–50.

Posma et al., "Effects of permanent dual chamber pacing on myocardial perfusion in symptomatic hypertrophic cardiomyopathy," *Heart* Oct. 1996;76(4):358–62.

Shen et al., "Survival and functional independence after implantation of a permanent pacemaker in octogenarians and nonagenarians. A population–based study," *Ann Intern Med* Sep. 15, 1996;125(6):476–80.

Irwin et al., "Long–term survival of chosen atrial–based pacing modalities," *Pacing Clin Electrophysiol* Nov. 1996;19(11 Pt 2):1796–8.

Glikson et al., "Short– and long–term results with an active–fixation, bipolar, polyurethane–insulated atrial pacing lead," *Pacing Clin Electrophysiol* Oct. 1996;19(10):1469–73.

Chachques et al., "Study of Muscular and Ventricular Function in Dynamic Cardiomyplasty: A Ten–Year Follow–up," *J. Heart Lung Transplant* 1997;16:854–68.

Lakkis et al., "Diagnosis of coronary artery disease by exercise thallium–201 tomography in patients with a right ventricular pacemaker," *J Am Coll Cardiol* May 1997;29(6):1221–5.

Mosseri et al., Coronary angiographic characteristics of patients with permanent artificial pacemakers, *Circulation* Aug. 5, 1997;96(3):809–15.

Aida et al., "Permanent pacemaker implantation in patients aged 80 years or older," *Kyobu Geka* May 1997;50(5):381–3 (English Abstract).

Giocolea et al., "Results of long–term permanent atrial stimulation in sick sinus disease," *Rev Esp Cardiol* Jul. 1997;50(7):474–9 (English Abstract).

Paxinos et al., "Long–term effect of VVI pacing on atrial and ventricular function in patients with sick sinus syndrome," *Pacing Clin Electrophysiol* Apr. 1998;21(4 Pt 1):728–34.

Nielsen et al., "Heart failure and echocardiographic changes during long–term follow–up of patients with sick sinus syndrome randomized to single–chamber atrial or ventricular pacing," *Circulation* Mar. 17, 1998;97(10):987–95.

Lamas et al., "Quality of life and clinical outcomes in elderly patients treated with ventricular packing as compared with dual–chamber pacing. Pacemaker Selection in the Elderly Investigators," *N Engl J Med* Apr. 16, 1998;338(16):1097–104.

Bohm et al., "Clinical observations with long–term atrial pacing," *Pacing Clin Electrophysiol* Jan. 1998;21(1 Pt 2):246–9.

Manolis et al., "Ventricular performance and quality of life in patients who underwent radiofrequency AV junction ablation and permanent pacemaker implantation due to medically refractory atrial tachyarrhythmias," *J Interv Card Electrophysiol* Mar. 1998;2(1):71–6.

Szabo et al., "Angina pectoris induced by pacemaker syndrome," *Orv Hetil* May 31, 1998;139(22):1357–60 (English Abstract).

Hefflin et al., "Final–year–of life pacemaker recipients," *J Am Geriatr Soc* Nov. 1998;46(11):1396–400 (English Abstract).

Greco et al., "Spinal Cord Stimulation for the Treatment of Refractory Angina Pectoris: A Two–Year Follow–Up," *Pace* 1999; 22[Pt. I]:26–32.

\* cited by examiner

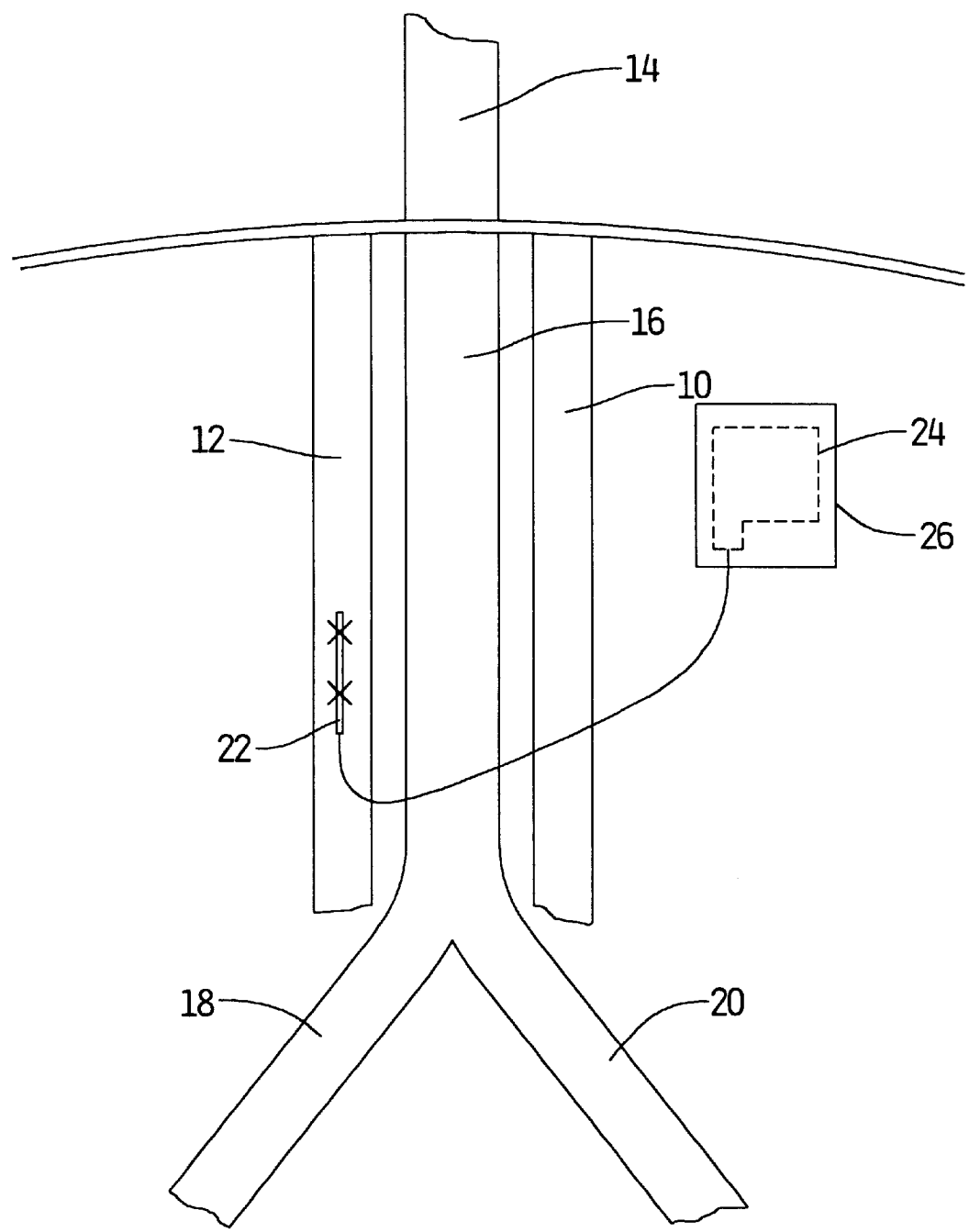
Fig_1

METHOD OF PREVENTION AND TREATMENT OF ATHEROSCLEROSIS AND ARTICLE OF MANUFACTURE THEREFOR

FIELD OF THE INVENTION

This application relates to a method of preventing and treating atherosclerosis, particularly to use of electrical stimulation to prevent or decrease atherosclerotic plaque formation in blood vessels.

BACKGROUND OF THE INVENTION

Atherosclerosis is an arterial disease characterized by the presence of plaque formed from the accumulation of fatty substances, cholesterol, calcium, fibrin and other cellular materials along the inner wall of the aorta and large and mediun-sized arteries. Plaque may totally or partially block blood flow through a blood vessel leading to a heart attack or stroke. Plaque can also weaken the arterial wall, resulting in an aneurysm. Coronary artery disease, which is usually due to atherosclerosis, is the leading cause of death in the world. Atherosclerosis is also a primary cause of stroke, another leading killer, and of peripheral vascular disease resulting in significant disability and limb loss.

Conventional therapies for treating the complications of atherosclerosis include providing an open bypass graft to other arteries by coronary or peripheral arterial bypass surgery, and dilating narrowed arteries by techniques such as balloon angioplasty, stent implantation, coronary atherectomy, and carotid endarterectomy. However, patients with severe diffuise disease in multiple vessels are not good candidates for surgery or dilating procedures. In addition, intracoronary procedures can stimulate a proliferation of endothelial cells at the treatment site, which leads to a reblockage of the artery. With laser techniques, intramyocardial channels can be created that will supply blood to the ischemic muscle and stimulate capillary in-growth and angiogenesis in the myocardium, however, there are accompanying risks of damage to the surrounding tissue. The long-term results of this procedure have been controversial. Furthermore, conventional therapies do not treat atherosclerosis directly to avoid its fatal complications.

Accordingly, an object of the invention is to provide an alternative method of preventing and treating atherosclerosis in a human patient.

SUMMARY OF THE INVENTION

These and other objects are achieved by the present invention, which provides a method of preventing, limiting and/or decreasing atherosclerotic plaque in blood vessels by creating an electrical field and/or applying low-frequency electrical stimulation to muscle tissue that is adjacent to or surrounds the vessel of interest.

The method provides a useful tool for disease prevention and treatment. The clinical applications of the present method assists persons at risk or suffering from ischemic heart disease, aortic atherosclerosis, peripheral vascular disease, cerebrovascular disease, and other similar disorders.

Advantageously, the present method can be used regardless of the percent blockage of the vessel or number of vessels affected, and does not traumatize the inner wall of the vessel. The method is also useful for preventing atherosclerosis development and for limiting and/or decreasing the progression of atherosclerosis in a patient with beginning or moderate atheroschlerosis.

BRIEF DESCRIPTION OF THE DRAWINGS

FIG. 1 is a schematic of one embodiment of the invention showing the implantation of a stimulator in the body of a patient to deliver electrical stimulation to the proas major muscle that lays close to the abdominal aorta.

DETAILED DESCRIPTION OF THE INVENTION

The present method provides a treatment for atherosclerosis that involves applying an electrical impulse externally to a blood vessel of interest at a particular rate and amplitude. The electrical impulse is applied indirectly to the blood vessel to effectively inhibit atherosclerotic plaque from becoming established or developing within the blood vessel, to inhibit existing plaque from increasing in size, and/or to decrease the size of existing plaque. The present method can be used to treat atherosclerosis in such blood vessels of the body as the abdominal aorta, carotid, femoral coronary, general peripheral arteries, among others.

According to the method, an electric impulse is applied to a muscle situated in close proximity to the blood vessel of interest, preferably adjacent to and/or surrounding the blood vessel. The electric impulse is effective to stimulate the muscle to contract and/or to generate an electrical field about the blood vessel, so as to inhibit and/or prevent the development of atherosclerotic plaque in the vessel.

The electrical impulse is generated by means of an electric pulse generator composed of a battery, electronic circuitry, and a connection outlet for a thin insulated wire or lead. Examples of electric pulse generators include pacemakers and cardiomyostimulators. The pulse generator can be implanted or used externally. The lead can be implanted near the vessel of interest, or positioned externally to apply the electric impulse through the skin to the target muscle and vessel. The pulse generator and leads can be implanted into the body of the patient by conventional techniques known in the art.

The pulse generator and lead can be positioned on opposite sides of the vessel being treated in order to create an electrical field about the vessel, or on the same side of the vessel for treatment without an electrical field. The electrical lead can be implanted into skeletal muscle close to and/or surrounding the vessel of interest in order to stimulate the muscle to contract, or outside the muscle into the connective tissue for treatment using an electrical field without muscle contraction. Preferably, the lead and pulse generator are positioned on opposite sides of the vessel being treated in order to create an electrical field around the vessel, with the lead implanted into a muscle surrounding the vessel. For example, in treating the abdominal aorta for atherosclerosis, the lead can be implanted into the psoas major muscle proximal to the abdominal aorta, and an electric pulse generator implanted in a subcutaneous muscle pocket on the opposite side of the aorta.

The pulse generator can be positioned externally on the skin to administer the electrical impulse through the skin to the target muscle and vessel. The lead can be implanted in the muscle, or applied on the skin surface when the targeted vessel is situated close to the skin surface. The electrical impulse that is generated by the pulse generator through the skin is effective to stimulate the target muscle and/or generate an electric field about the vessel.

The electrical impulse applied to the target muscle causes the muscle to contract at a desired pace. The electrical impulse is preferably a low frequency impulse of about 2–20 Hz, preferably about 5–15 Hz, more preferably about 8–10 Hz, at an amplitude of about 1–6 V, preferably about 2–4 V, more preferably about 2.5–3.0 V. The electrical impulse can be emitted at a rate of 30–120 beats per minute, preferably about 40–80 beats, preferably about 50–60 beats. Preferably, the electric pulse generator is programmable and can also be altered as desired during treatment as to the rate and amplitude of the electrical impulse that is emitted. It has been shown that applying the prescribed electrical impulse for an effective time period of between about 8–10 weeks, can reduce the level of atherosclerosis in the abdominal aorta of a rabbit from about 3–4+ to about 0–2+, where 4+ is the highest level.

The application of the electrical impulse and the treatment period are effective for achieving the desired effect on atherosclerotic plaque in the target vessels. The periodicity of applying the electrical impulse and length of time for treatment are determined according to the level of atheroschlerosis in the treated vessel. The electrical impulse can be applied continuously or at intervals during the treatment period. Treatment time and periodicity can be varied and treatment can be repeated if necessary. For treatment of a blood vessel with beginning atherosclerosis, electrical stimulation of the muscle is preferably maintained for at least about 8 weeks and up to about 16 weeks, preferably about 8–10 weeks. In disease prevention, a person can be assessed as to the level of risk for developing atherosclerosis such as by taking a family history, and electrical stimulation can be applied according to the invention to prevent development of the disease. Prevention treatment time and periodicity can be varied based on risk factors and the results of monitoring plaque development.

To monitor the treatment process, the size and extent of atherosclerotic plaque in the vessel can be measured before applying the electrical impulse and monitored during and/or after treatment. Coronary or peripheral vessels can be observed by conventional clinical imaging techniques, including, for example, intravascular ultrasound, magnetic resonance imaging (MRI), radiography, computed tomography (CT), cardiac positron emission tomography (PET), digital cardiac or subtraction angiography (DCA, DSA), single photon emission computed tomography (SPECT) myocardial perfusion imaging, and coronary arteriography.

Also provided is a system for treating atherosclerosis composed of a member for generating an electrical impulse that can be implanted in the body or used externally, and an electrical lead or leads that are either implanted into the muscle or connective tissue proximal to the vessel or applied externally to the skin to create an electrical field and/or to convey the electric impulse to the superficial muscle to stimulate muscle contraction. The pulse generator can be programmed to generate a low-frequency electrical impulse, preferably of about 8–10 Hz at about 50–60 beats per minute, and an amplitude of about 2.5–3.0 V.

The system can be packaged together as an article of manufacture or kit for use in treating atherosclerosis in a patient, along with instructions for the use of the system, including implanting the system into the patient, external placement of the system on the body of the patient, and programming the pulse generator.

The invention will be further described by reference to the following detailed examples, wherein the methodologies are described below. These examples are not meant to limit the scope of the invention that has been set forth in the foregoing description. Variation within the concepts of the invention is apparent to those skilled in the art. The disclosures of the cited references throughout the application are incorporated by reference herein.

EXAMPLE 1

Time Period for Development of Atherosclerosis

A group of rabbits were subjected to a high cholesterol diet over varying time periods to determine the development of atherosclerosis.

Series I: High Cholesterol Diet for 3 Weeks Without Electrical Stimulation

A control group of four rabbits was placed on a 3-week high cholesterol diet to investigate the beginning of the atherosclerosis process.

After three weeks, there was evidence of the beginning of atherosclerosis. Serum cholesterol levels increased from a normal range of 132–373 mg/dL to 498–1020 mg/dL. The level of atherosclerosis was as follows.

| coronary arteries | aortic root | top of abdominal aorta | bottom of abdominal aorta | spleen |
|---|---|---|---|---|
| 2.5+ | 3.0+ | 0.7+ | 1.0+ | 1.5+ |

Series II: High Cholesterol Diet for 8 Weeks Without Electrical Stimulation

A control group of three rabbits was placed on an 8-week high cholesterol diet to investigate the advanced atherosclerosis process. After eight weeks, the three rabbits showed evidence of moderate atherosclerosis. Serum cholesterol levels increased to 894–1413 mg/dl. The level of atherosclerosis was as follows.

| coronary arteries | aortic root | top of abdominal aorta | bottom of abdominal aorta | spleen |
|---|---|---|---|---|
| 3.1+ | 3.2+ | 1.2+ | 1.5+ | 2.4+ |

Series III: High Cholesterol Diet for 11–12 Weeks Without Electrical Stimulation A control group of seven rabbits was placed on a 11–12 week high cholesterol diet to investigate advanced atherosclerosis.

After 11–12 weeks, there was evidence of very advanced atherosclerosis. Serum cholesterol reached 1111–1954 mg/dl. The levels of atherosclerosis were as follows.

| coronary arteries | aortic root | top of abdominal aorta | bottom of abdominal aorta | spleen |
|---|---|---|---|---|
| 3.5+ | 3.8+ | 3.3+ | 3.0+ | 2.8+ |

EXAMPLE 2

Determination of Rate and Amplitude of Electrical Stimulation

Electrical stimulation was applied to the psoas major muscle close to the abdominal aorta of rabbits on a high cholesterol diet (HCD) to assess the effect on the development of atherosclerosis. An optimal rate and amplitude of electrical stimulation to modify the atherosclerotic process in the abdominal aorta was determined as follows.

A 12-week high cholesterol diet was used in twelve rabbits to create a model of atherosclerosis. After four weeks of the high cholesterol diet, a pacemaker and an electrical lead were implanted in each of the twelve rabbits of the experimental group, as illustrated in FIG. 1. As shown, the right and left psoas major muscles 10, 12, are located on either side of the thoracic aorta 14, and the abdominal aorta 16 which leads to the right and left iliac arteries 18, 20. An electrode 22 was sutured to the left psoas major muscle 12. A pacemaker 24 was implanted in the muscle pocket 26 on the opposite side near the right psoas major muscle 10. Immediately following implantation, the pacemaker 24 was started with 10 Hz electrical stimulation applied to the psoas major muscle 12 and continued for eight weeks.

Experiments were conducted at impulse rates of 60 beats per minute (bpm) and 4.0 V (series IV), impulse rates of 60 bpm and 2.0 V (series V), and impulse rates of 120 bpm and 4.0 V (series VI). The control was the series III rabbits from Example 1. Diet was continued in both the control and experimental groups. Blood lipid levels were assayed throughout the eight-week stimulation period.

At the end of the 12-week high cholesterol diet and eight weeks of stimulation, all rabbits were euthanized. Autopsy studies examined the morphology of the abdominal and thoracic aortas, the heart, the coronary artery system, the liver and the spleen.

The test rabbits (series IV–VI) were compared to the control rabbits (series III) from Example 1. The results are shown in the following table.

|  | coronary arteries | aortic root | top of abdominal aorta | bottom of abdominal aorta | spleen |
| --- | --- | --- | --- | --- | --- |
| Control Series III (Ex. 1) | 3.5+ | 3.8+ | 3.3+ | 3.0+ | 2.8+ |
| Series IV 60 bpm 4V | 3.3+ | 3.5+ | 0.5+ | 0.6+ | 2.9+ |
| Series V 60 bpm 2V | 3.7+ | 3.6+ | 2.5+ | 2.6+ | 2.7+ |
| Series VI 120 bpm 4V | 3.5+ | 3.1+ | 2.1+ | 2.7+ | 3.1+ |

In all the test rabbits, there was evidence of very advanced atherosclerosis, that is, serum cholesterol reached 998–1876 mg/dL. The level of atherosclerosis in the spleens was 2.7–3.1+, in the coronary arteries 3.3–3.7+, and in the aortic roots 3.1–3.6+.

In the abdominal aortas, the evidence of atherosclerosis was different between the test groups. In the control rabbits (series III, Example 1) in which there was no electrical stimulation, the level of atherosclerosis was measured at 3.3+ in the top of abdominal aorta and at 3.0+ in the bottom. When a rate of 60 beats per minute (bpm) and 4.0 V were applied (series IV), the level of atherosclerosis was 0.5+ in the top of the abdominal aorta and 0.6+ in the bottom of the abdominal aorta. At 2.0 V and the same rate of 60 bpm (series V), the level of atherosclerosis in the top and bottom of the abdominal aorta was 2.5+ and 2.6+, respectively, which was less than in the control group (series III, Example 1) but more than in the series IV test group. When 120 bpm was used at 4.0 V (series VI), the level of atherosclerosis in the abdominal aorta was also greater than in the test series IV, at 2.1+ (top) and 2.7+ (bottom).

The results indicate that electrical stimulation inhibited the development of atherosclerotic plaque in the treated rabbits, whereas the control group developed advanced atherosclerosis on the high cholesterol diet.

Based on those results, the optimal rate and amplitude of electrical stimulation for modifying the development of atherosclerosis was determined to be 60 beats per minute and 4.0 V. In a human application, initial cholesterol levels and arterial lesions could be observed, and a similar test procedure could be followed in which electrical stimulation could be applied by various methods to verify the optimal rate and amplitude of electrical stimulation.

EXAMPLE 3

Electrical Stimulation Applied to Beginning Atherosclerosis

The results of the series I control investigation in Example 1 indicated that after 3–4 weeks of a high cholesterol diet, there was the beginning of atherosclerosis at a level of 0.7+ and 1.0+ at the top and bottom of the abdominal aorta, respectively. In the following investigation, electrical stimulation was applied around the abdominal aorta for an eight week period beginning at week 3–4, to determine the effect on the atherosclerotic process in conjunction with a high cholesterol diet.

In the series III control group (Example 1) that was subjected to 11–12 weeks high cholesterol diet (no electrical stimulation), the level of atherosclerosis increased to 3.3+ in the top of the abdominal aorta and to 3.0+ in the bottom of the abdominal aorta.

The control (series III) was compared to the series IV test animals (Example 2) that were subjected to a 12-week high cholesterol diet with electrical stimulation at 60 bpm and 4.0 V during weeks 4–12, and a series VII group of four rabbits subjected to 12-weeks of a high cholesterol diet with electrical stimulation at 30 bpm and an amplitude of 2.5–3.0V during weeks 4–12. The results showed that electrical stimulation did not alter the cholesterol level in the test group rabbits, which varied between 1385–1851 mg/dL after eleven weeks of HCD. The cholesterol level in the control group rabbits was 1111–1954 mg/dL after eleven weeks of HCD. The levels of atherosclerosis were as follows.

|  | coronary arteries | aortic root | top of abdominal aorta | bottom of abdominal aorta | spleen |
| --- | --- | --- | --- | --- | --- |
| Control Series III (Ex. 1) | 3.5+ | 3.8+ | 3.3+ | 3.0+ | 2.8+ |
| Series IV 60 bpm 4.0 V (Ex. 2) | 3.3+ | 3.5+ | 0.5+ | 0.6+ | 2.9+ |
| Series VII 30 bpm 2.5–3.0 V | 2.6+ | 3.4+ | 0.5+ | 0.6+ | 2.3+ |

These data also showed that electrical stimulation, when applied in the beginning stages of the atherosclerotic process, inhibited its development (0.5–0.6+) compared with the control series (3.0+–3.3+).

EXAMPLE 4

Electrical Stimulation Applied to Moderate Atherosclerosis

The investigation in Example 1 showed that after 8 weeks of high cholesterol diet, the series II (control) group had a level of atherosclerosis of 1.2+ in the top of the abdominal aorta and 1.5+ in the bottom of aorta.

In the present example, four rabbits (series VIII, control) were placed on an 8-week high cholesterol diet and then on a normal diet for another eight weeks. A separate group of 4 rabbits were also put on the normal diet but with electrical stimulation of 30 bpm and 2.5–3V for an 8-week period from weeks 9–16. In the series II control rabbits (Example 1), the level of atherosclerosis in the top and bottom of the abdominal aorta was approximately the same as in the series VIII control rabbits after 8 weeks of high cholesterol diet. In the series IX test rabbits which were subjected to electrical stimulation, there was only a trace of atherosclerosis.

|  | coronary arteries | Aortic root | top of abdominal aorta | bottom of abdominal aorta | spleen |
|---|---|---|---|---|---|
| Control (Series II, Ex. 1) 8 wks. HCD | 3.1+ | 3.2+ | 1.2+ | 1.5+ | 2.4+ |
| Control Series VIII 8 wks. HCD + 8 wks. normal diet | 2.8+ | 3.0+ | 1.0+ | 1.2+ | 2.6+ |
| Series IX 8 wks. HCD + 8 wks. normal diet & electr. stimul. at 30 bpm, 2.5–3 V | 2.7+ | 3.1+ | 0.3+ | 0.4+ | 2.4+ |

In all rabbits after 8–11 weeks (with and without electrical stimulation), the spleen contained fat deposits, fatty macrophages, and focal infarctions. The aortic root had 2+ to 4+ atheroma and, occasionally, calcification with extensive myocardial fibrosis, along with traces of necrosis extending toward the base of the heart. Intramyocardial vessels showed similar evidence of advanced atherosclerosis. When applied around the abdominal aorta, the electrical stimulation did not influence the spleen, heart, and root of the aorta. All of these areas were outside the field of electrical stimulation.

The levels of atherosclerosis of the abdominal aorta, the area subjected to the electrical stimulation field, were intriguingly different between the control and experimental rabbits, as indicated in the above tables.

In all rabbits without electrical stimulation, the level of atherosclerosis in the abdominal aorta was between 2.5+ and 4.0+. In contrast, in all rabbits with electrical stimulation, there was no evidence or only a trace (0.3–0.6+) of atherosclerosis in the abdominal aorta. These results show the direct influence of low-frequency electrical stimulation on preventing (series VII and IV) and treating (series IX) the atherosclerotic process.

What is claimed is:

1. A method of treating atherosclerosis, comprising:
applying an electrical impulse proximal to a blood vessel of a person, at a rate and amplitude effective to inhibit the development of an atherosclerotic plaque in the vessel.

2. The method of claim 1, comprising: applying the electrical impulse to a muscle proximal to the blood vessel to cause the muscle to contract.

3. The method of claim 2, comprising: applying the electrical impulse to stimulate the muscle to contract at a rate of about 30–120 beats per minute.

4. The method of claim 2, comprising: applying the electrical impulse to stimulate the muscle to contract at a rate of about 30–60 beats per minute.

5. The method of claim 1, comprising: generating an electrical field around the blood vessel.

6. The method of claim 1, further comprising: implanting at least one of an electric pulse generator and an electrical lead into the body of the person in proximity to the blood vessel.

7. The method of claim 4, further comprising: modifying the rate and amplitude of the electrical impulse.

8. The method of claim 1, further comprising: placing at least one of an electric pulse generator and an electrical lead external to the body of the person.

9. The method of claim 1, further comprising:
implanting an electrical lead to an electric pulse generator into the muscle on one side of the blood vessel;
implanting the electric pulse generator on an opposite side of the blood vessel; and
generating the electrical impulse from the electric pulse generator through the electrical lead into the muscle.

10. The method of claim 1, further comprising:
implanting an electrical lead to an electric pulse generator into a muscle on one side of the blood vessel;
implanting the pulse generator on the same side of the blood vessel as the electric lead; and
generating the electrical impulse from the electric pulse generator through the electrical lead into the muscle.

11. The method of claim 1, further comprising:
implanting an electrical lead to an electric pulse generator into connective tissue proximal to the blood vessel;
implanting the electric pulse generator on an opposite side of the blood vessel; and
generating an electrical current flow from the electric pulse generator through the electrical lead, wherein an electric field is created around the vessel.

12. The method of claim 1, further comprising:
positioning an electrical lead to an electric pulse generator on the skin of the patient and in proximity to the muscle;
positioning the electric pulse generator external to the skin of the patient and in proximity to the vessel; and
generating an electrical current flow from the electric pulse generator through the electrical lead and the skin of the patient to the muscle.

13. The method of claim 1, comprising: applying the electrical impulse to effectively decrease the size of the atherosclerotic plaque.

14. The method of claim 1, comprising: applying a low frequency electrical impulse of about 2–20 Hz and an amplitude of about 1–6 V.

15. The method of claim 1, comprising: applying a low frequency electrical impulse of about 8–10 Hz and an amplitude of about 2.5–3.0 V.

16. The method of claim 1, comprising: applying the electrical impulse at intervals during a treatment period.

17. The method of claim 1, further comprising: measuring and comparing the size of the atherosclerotic plaque in the blood vessel before and after applying the electrical impulse.

18. The method of claim 1, further comprising: measuring and comparing the blood flow through the blood vessel before and after applying the electric impulse.

19. The method of claim 1, comprising: applying the electrical impulse to reduce the atherosclerotic plaque by about 25–95%.

20. The method of claim 1, comprising: applying the electrical impulse to reduce the atherosclerotic plaque by about 75–90%.

21. The method of claim 1, comprising: applying the electrical impulse to increase bloodflow through the blood vessel by about 25–50%.

22. The method of claim 1, wherein the blood vessel is selected from the group consisting of abdominal aorta, coronary artery, thoracic aorta, femoral artery, and a peripheral artery.

23. A system for treating atheroschlerosis according to the method of claim 1, comprising:
   a) a member for generating an electrical impulse and programmed to generate a low-frequency electrical impulse of about 2–20 Hzat about 30–120 beats per minute, and an amplitude of about 1–6 V; and
   b) an electrical lead for transmitting the electrical impulse proximal to a blood vessel being treated.

24. The system of claim 23, wherein the pulse generating member is programmed to generate a low-frequency electrical impulse of about 8–10 Hz and an amplitude of about 2.5–3.0 V.

25. The system of claim 23, wherein at least one of the pulse generating member and the electric lead is implantable in the body of the patient.

26. The system of claim 23, wherein at least one of the pulse generating member and the electric lead can be applied externally to the skin of the patient.

27. The system of claim 23, wherein the pulse generating member is operable to be reprogrammed to modify the rate and amplitude of the generated electrical impulse.

28. A method of treating atherosclerosis, comprising:
   applying an electrical impulse to a muscle proximal to a blood vessel of a person, at a rate and amplitude effective to stimulate contraction of the muscle and generate an electric field around the vessel, and inhibit the development of an atherosclerotic plaque in the vessel.

29. A method of preventing atherosclerosis, comprising:
   applying an electrical impulse proximal to a blood vessel of a person, at a rate and amplitude effective to prevent the development of an atherosclerotic plaque in the vessel.

30. The method of claim 24, comprising: applying the electrical impulse at a rate and amplitude effective to generate an electrical field around the blood vessel.

31. The method of claim 24, comprising: applying the electrical impulse to a muscle proximal to the blood vessel at a rate and amplitude effective to cause the muscle to contract, to generate an electrical field around the blood vessel, or both.

32. A method of decreasing an atherosclerotic plaque in a vessel of a person, comprising: subjecting an area of atherosclerotic plaque in a blood vessel to a low-frequency electrical impulse at a rate and amplitude effective to decrease the size of the plaque in the vessel.

33. The method of claim 27, comprising: applying the electrical impulse at a rate and amplitude effective to generate an electrical field around the blood vessel.

34. The method of claim 27, comprising: applying the electrical impulse to a muscle proximal to the blood vessel at a rate and amplitude effective to cause the muscle to contract, to generate an electrical field around the blood vessel, or both.

35. An article of manufacture, packaged together, for use for treating atherosclerosis in a patient, comprising:
   a) a member for generating an electrical impulse and programmable to generate a low-frequency electrical impulse of about 2–20 Hz and an amplitude of about 1–6 V;
   b) an electrical lead for transmitting the electrical impulse proximal to a blood vessel being treated in the body; and
   c) instructions for use of the pulse generating member and the electric lead in treating atherosclerosis according to the method of claim 1.

36. The article of claim 35, wherein at least one of the pulse generating member and the electric lead is implantable in the body of the patient.

37. The system of claim 35, wherein at least one of the pulse generating member and the electric lead can be applied externally to the skin of the patient.

* * * * *